United States Patent
Wang-Zhang et al.

(10) Patent No.: US 11,021,442 B2
(45) Date of Patent: Jun. 1, 2021

(54) PROCESS FOR THE PREPARATION OF FREEZE-DRIED 2-[(3-AMINOPROPYL)AMINO]ETHANETHIOL FORMULATION

(71) Applicants: CLEVEXEL PHARMA, Paris (FR); INSTITUT GUSTAVE ROUSSY, Villejuif (FR)

(72) Inventors: Xiuping Wang-Zhang, Paris (FR); Perrine Pivette, Alfortville (FR); Karine Gonzalez, Maisons Alfort (FR); Eric Deutsch, Paris (FR); Céline Clemenson, Orsay (FR)

(73) Assignees: CLEVEXEL PHARMA, Paris (FR); INSTITUT GUSTAVE ROUSSY, Villejuif (FR)

( * ) Notice: Subject to any disclaimer, the term of this patent is extended or adjusted under 35 U.S.C. 154(b) by 86 days.

(21) Appl. No.: 16/465,505

(22) PCT Filed: Nov. 29, 2017

(86) PCT No.: PCT/EP2017/080881
§ 371 (c)(1),
(2) Date: May 30, 2019

(87) PCT Pub. No.: WO2018/100008
PCT Pub. Date: Jun. 7, 2018

(65) Prior Publication Data
US 2020/0239414 A1    Jul. 30, 2020

(30) Foreign Application Priority Data
Nov. 30, 2016 (EP) .................................. 16306582

(51) Int. Cl.
*C07C 323/25* (2006.01)
*A61P 17/02* (2006.01)
*A61K 9/06* (2006.01)
*A61K 9/19* (2006.01)

(52) U.S. Cl.
CPC .............. *C07C 323/25* (2013.01); *A61K 9/06* (2013.01); *A61K 9/19* (2013.01); *A61P 17/02* (2018.01)

(58) Field of Classification Search
CPC .......... C07C 323/25; A61K 9/06; A61K 9/19; A61P 17/02
USPC ....................................................... 568/69
See application file for complete search history.

(56) References Cited

U.S. PATENT DOCUMENTS 6,239,119 B1    5/2001    Stogniew et al.
6,407,278 B2    6/2002    Stogniew et al.

FOREIGN PATENT DOCUMENTS

SU    670 567 A1    6/1979

OTHER PUBLICATIONS

Walker et al., "WR1065 Mitigates AZT-ddI-Induced Mutagenesis and Inhibits Viral Replication," Environmental and Molecular Mutagenesis, 2009, vol. 50, pp. 460-472.
Troev et al., "Immobilization of Aminothiols on Poly(oxyethylene H-phosphonate)s and Poly(oxyethylene phosphate)s—An Approach to Polymeric Protective Agents for Radiotherapy of Cancer," Journal of Polymer Science, Part A: Polymer Chemistry, 2007, vol. 45, pp. 1349-1363.
DeLuca et al., "Lyophilization of Pharmaceuticals I," Journal of Pharmaceutical Sciences, Apr. 1965, vol. 54, No. 4, pp. 617-624.
Mar. 8, 2018 International Search Report issued in International Patent Application No. PCT/EP2017/080881.

*Primary Examiner* — Jeffrey H Murray
(74) *Attorney, Agent, or Firm* — Oliff PLC

(57) ABSTRACT

A process for the preparation of freeze-dried 2-[(3-aminopropyl)amino]ethanethiol including the following steps: a) the reaction of a solution of amifostine with a strong acid, to obtain a solution of 2-[(3-aminopropyl)amino]ethanethiol, and b) the freeze-drying of the solution of 2-[(3-aminopropyl)amino]ethanethiol, with or without addition of excipients.

16 Claims, 4 Drawing Sheets

Figure 1:
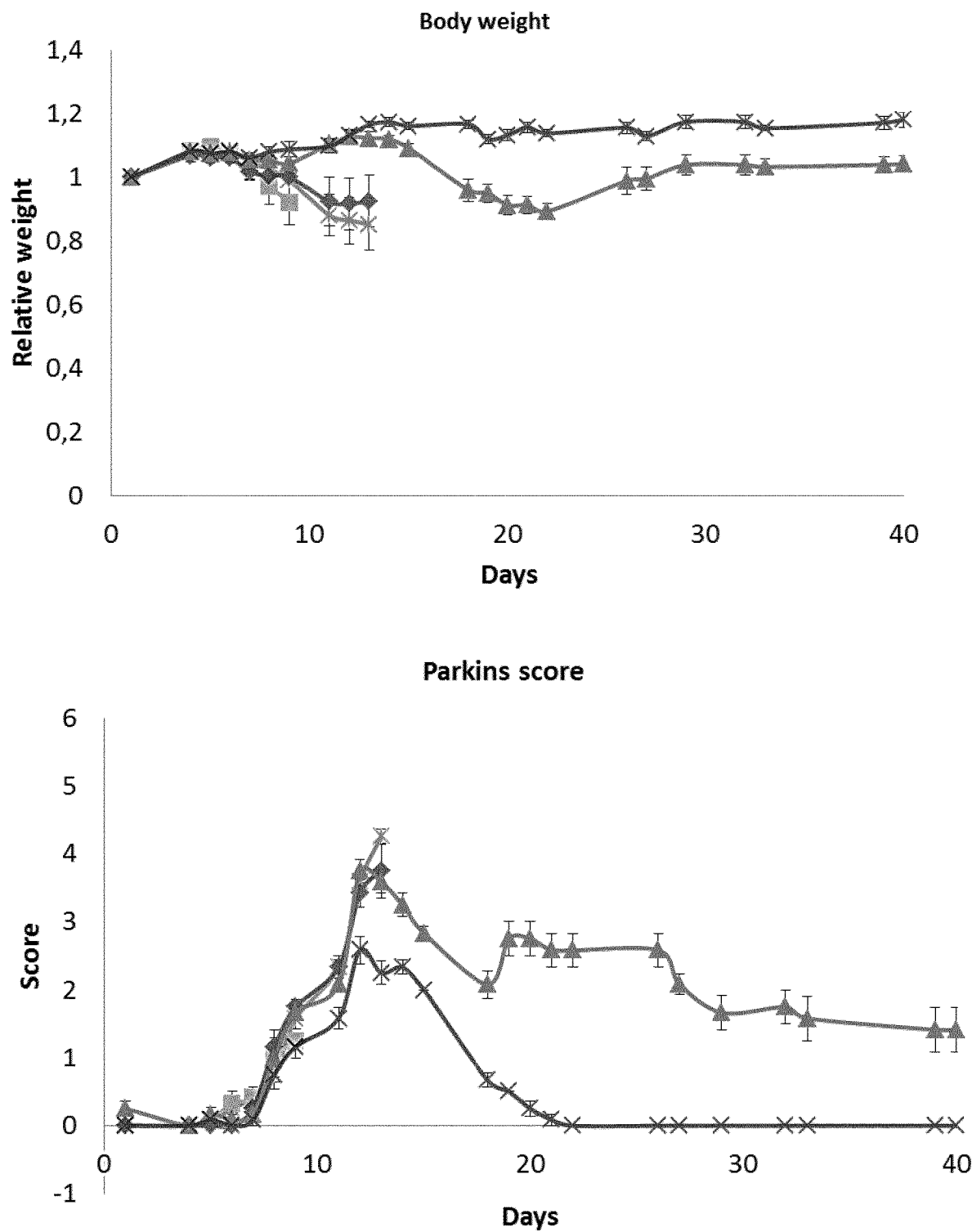

PROCESS FOR THE PREPARATION OF FREEZE-DRIED 2-[(3-AMINOPROPYL)AMINO]ETHANETHIOL FORMULATION

The present invention concerns a process for the preparation of freeze-dried 2-[(3-aminopropyl)amino]ethanethiol formulation, as well as the corresponding lyophilisate such as obtained by said process.

Amifostine is a phosphorylated prodrug that is converted into free active 2-[(3-aminopropyl)amino]ethanethiol (aminothiol) under the action of the alkaline phosphatase. Presently, amifostine is delivered intravenously but important adverse effects are associated with the administration route (hypotension, nausea . . . ). Oral route administration of amifostine has been tested in both animal and in humans but studies showed that amifostine and aminothiol are poorly absorbed mainly due to significant degradation in the gastrointestinal tract (Kouvaris J R et al, Amifostine: the first selective-target and broad spectrum radioprotector. The Oncologist 2007; 12:738-747).

Amifostine is currently marketed in various countries as Ethyol®, a sterile lyophilized powder for IV perfusion for the following indications:
- reduction of the cumulative renal toxicity associated with repeated administration of cisplatin in patients with advanced ovarian cancer, and
- reduction of the incidence of moderate to severe xerostomia in patients undergoing post-operative radiation treatment for head and neck cancer, where the radiation port includes a substantial portion of the parotid glands.

U.S. Pat. No. 6,239,119 discloses methods of treating or protecting mucosal tissue from damage associated with radiation and/or chemotherapeutic treatment of cancers, by the topical application of amifostine and related compounds. It also discloses the treatment and prevention of infections associated with mucositis by topical application of amifostine and related compounds.

Until now, there is no stable thermogel formulation comprising amifostine or a derivative thereof efficient for treating radiation-induced oral mucositis.

The aim of the present invention is to prepare a stable topical formulation for chemo-radioprotection, comprising 2-[(3-aminopropyl)amino]ethanethiol, which adheres to the mucous membranes or on the skin.

Another aim of the present invention is to provide a process for the preparation of stable freeze-dried 2-[(3-aminopropyl)amino]ethanethiol, with or without the presence of excipients.

Another aim of the present invention is to provide stable freeze-dried 2-[(3-aminopropyl)amino]ethanethiol formulated or to be formulated in a thermosensitive gel for treating radiation-induced mucositis.

Another aim of the present invention is to provide stable freeze-dried 2-[(3-aminopropyl)amino]ethanethiol formulated or to be formulated in a thermosensitive gel for treating radiation-induced cutaneous erythema.

The present invention relates to a process for the preparation of freeze-dried 2-[(3-aminopropyl)amino]ethanethiol, in particular of stable freeze-dried 2-[(3-aminopropyl)amino]ethanethiol, with or without the presence of excipients, comprising the following steps:
a) the reaction of a solution of amifostine with a strong acid, to obtain a solution of 2-[(3-aminopropyl)amino]ethanethiol, and
b) the freeze-drying of the solution of 2-[(3-aminopropyl)amino]ethanethiol, with or without addition of excipients.

The present invention also relates to a process for the preparation of a freeze-dried 2-[(3-aminopropyl)amino]ethanethiol formulation, with or without the presence of excipients, comprising the steps as mentioned above.

The process of preparation according to the invention has the advantage of increasing the stability of the obtained freeze-dried 2-[(3-aminopropyl)amino]ethanethiol.

Preferably, the obtained freeze-dried 2-[(3-aminopropyl)amino]ethanethiol contains preferably less than 5%, more preferably less than 2%, and still more preferably less than 1% (area %) of disulfide (or any other impurities) by weight in relation to the total weight of said product, upon storage over a given period in ICH (International Council for Harmonization of Technical Requirements for Pharmaceutical for Human Use) conditions.

Preferably, the freeze-dried 2-[(3-aminopropyl)amino]ethanethiol (or aminothiol) is in the form of a salt. As shown below, the use of the strong acid for the conversion of amifostine into aminothiol gives a salt.

In particular, when using hydrochloric acid, this conversion step may be represented as follows:

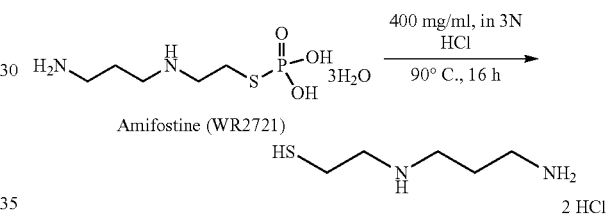

According to the invention, the solution of amifostine comprises is an amifostine acidic solution.

According to the invention, the term "strong acid" refers to an acid that completely ionizes in a solution. Within the present application, it refers to any acid widely used in the pharmaceutical field. Preferably, a strong acid according to the invention has a pKa equal to or less than 2.0.

Preferably, the strong acid is chosen from the group consisting of: hydrochloric acid, phosphoric acid, sulfuric acid, and mixtures thereof. Most preferably, the strong acid is hydrochloric acid.

The aim of step a) as defined above is to obtain a conversion as complete as possible together with the smallest amount of impurities. The obtained solution of aminothiol has thus a high purity.

According to a preferred embodiment, step a) as defined above involves the reaction of a solution of amifostine with hydrochloric acid.

According to a preferred embodiment, step a) is carried out at a temperature comprised between 50° C. and 90° C.

Below 50° C., the conversion process is too long (especially for more than 24 h) and the yield of aminothiol is less than 90%. Above 90° C., the conversion process is accelerated, but new unknown impurities are formed.

Preferably, step a) is carried out at a temperature comprised between 50° C. and 70° C., and most preferably at a temperature equal to 60° C.

According to a preferred embodiment, step a) is carried out for 30 minutes to 24 hours.

Below 30 minutes, the conversion is not complete, the yield of aminothiol being less than 90%. Above 24 hours, new unknown impurities are formed.

Preferably, step a) is carried out for one hour.

According to a preferred embodiment, the concentration of amifostine is comprised between 80 mg/ml and 500 mg/ml.

Below a concentration of amifostine of 80 mg/ml, it is advantageous to carry out a dilution step, in particular the dilution step a1) as explained below.

Above a concentration of amifostine of 500 mg/ml, the process is difficult to be implemented because of the solubility of amifostine.

Preferably, the concentration of amifostine is equal to 500 mg/ml.

According to a preferred embodiment, the molarity of the acid (or its molar concentration) is comprised between 1M and 4M.

For a molarity of the acid below 1M, the conversion process may be too long and the yield of aminothiol is less than 90%.

For a molarity of the acid above 4M, the final pH of the resulting thermogel would be too low (pH≤4.0) and thus the thermogel would not suitable for its administration. Thus, it would be necessary to carry out another step of pH adjustment.

Preferably, the molarity of the acid is equal to 4 M.

According to an embodiment, the molar ratio between the amount of amifostine and the amount of acid is comprised between 1:0.5 and 1:3, and preferably between 1:0.5 and 1:2.

When the molar ratio is less than 1:0.5, the conversion process is too long and the yield of aminothiol is less than 90%.

When the molar ratio is above 1:3, the final pH of the resulting thermogel would be too low (pH≤4.0) and thus the thermogel would not suitable for its administration and another step of pH adjustment should be added to the manufacturing process.

Step b) is a freeze-drying step, also known as lyophilization or cryodesiccation. This step involves the freezing of the solution of 2-[(3-aminopropyl)amino]ethanethiol, with or without the presence of excipients such as penetration enhancers, taste masking as aromas and sweeteners, mucoadhesive agents, co-solvents, humectants, colouring agents and other functional excipients as poloxamers, and then the reduction of the surrounding pressure to allow the frozen water in the material to sublimate directly from the solid phase to the gas phase.

Preferably, for this freeze-drying step, several parameters are to be considered: the freezing rate, the shelf freezing temperature and the shelf temperature of primary drying.

According to a preferred embodiment, the freezing rate should be high. Preferably, this freezing rate is of about 1.6° C. per minute during a step of 40 minutes. This high freezing rate makes possible to avoid the formation of a 'skin' (or 'shell') on the surface of the lyophilisate due to the high concentration of acidic solute excluded by the ice matrix during the freezing.

According to a preferred embodiment, the shelf freezing temperature is low. Preferably, the shelf freezing temperature is of about −60° C., in order to freeze all the acidic aminothiol solution before the sublimation.

According to a preferred embodiment, the shelf temperature of primary drying is low. Preferably, the shelf temperature of primary drying is less than −40° C., in order to avoid the melting of the product. During the first step of primary drying, the product temperature is less than the melting temperature of the product.

The process according to the invention may further comprise a step a1), after step a) and before step b), for diluting the solution of 2-[(3-aminopropyl) amino]ethanethiol, with or without addition of excipients in the solution.

Step a1) consists preferably in the addition of an aqueous solution comprising water or at least one poloxamer into the solution of 2-[(3-aminopropyl) amino]ethanethiol.

Preferably, step a1) consists in the addition of an aqueous solution comprising at least one poloxamer into the solution of 2-[(3-aminopropyl)amino]ethanethiol.

Poloxamers (commercial names: Pluronics®, Lutrol®, Kolliphor®), are non-ionic block copolymers of ethylene oxide (EO) and propylene oxide (PO) synthesized by sequential addition of propylene oxide first and then ethylene oxide to a low molecular weight water-soluble propylene glycol (Thermosensitive Self-Assembling Block Copolymers as Drug Delivery Systems. G. Bonacucina, M. Cespi, G. Mencarelli, G. Giorgiono and G. F. Palmieri. *Polymers* 2011, 3, 779-811).

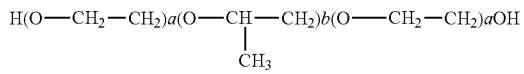

Preferably, the poloxamers used in the present invention are Poloxamer 407, Poloxamer 188, and mixtures thereof.

Poloxamer 407 is a commonly used co-polymer in pharmaceutical topic formulations.

A mixture of Poloxamer 407 and Poloxamer 188 is widely used in pharmaceutical application for the thermosensitive property. The combination of the two grades of Poloxamers-407 and 188 allows targeting several sol-gel temperatures transition.

At constant Poloxamer 407 concentration, increasing the Poloxamer 188 concentration gradually increased the sol-gel temperature transition, initially to a maximum, and then it decreased.

The present invention also relates to a lyophilisate, in particular a stable lyophilisate, of 2-[(3-aminopropyl)amino] ethanethiol susceptible to be obtained according to the process as defined above.

The present invention also relates to a process for the preparation of a thermogel composition of 2-[(3-aminopropyl)amino]ethanethiol, in particular a stable thermogel composition of 2-[(3-aminopropyl)amino]ethanethiol, comprising the reconstitution of the lyophilisate as defined above with an aqueous solution.

According to the invention, a thermosensitive gel is an in-situ forming system which is liquid before administration, for example at room temperature or at 5° C.±3° C., and which jellifies upon heating conditions. After cooling, this system becomes liquid again.

The aqueous solution used for this reconstitution step may comprise water and/or poloxamers as defined above.

Preferably, this aqueous solution is constituted by water when the freeze-dried aminothiol has been prepared by a process comprising the implementation of a step a1) as defined above involving the dilution with a solution comprising at least one poloxamer.

Preferably, this aqueous solution comprises at least one poloxamer when the freeze-dried aminothiol has been prepared by a process comprising the implementation of a step a1) as defined above involving the dilution with water only.

Preferably, in this aqueous solution, other excipients could be added for the following, but not limited, purposes: penetration enhancers such as Transcutol® (diethylene glycol monoethyl ether), taste masking as aromas and sweeteners, mucoadhesive agents, co-solvents, humectants, colouring agents and other functional excipients.

Preferably, the aqueous solution for the reconstitution step further comprises aromas, such as mint aroma and/or bitter maskers, and/or other excipients such as penetration enhancer For example, the aqueous solution for the reconstitution step of the freeze-dried aminothiol contains a mint flavor, a bitter masker and water, preferably in the following respective amounts: 4%, 0.05% and 95.95% w/w/w.

The present invention also relates to a thermogel composition of 2-[(3-aminopropyl)amino]ethanethiol susceptible to be obtained according to the process as defined above.

The present invention also relates to the thermogel composition of 2-[(3-aminopropyl)amino]ethanethiol as mentioned above, for its use for treating radiation-induced oral mucositis.

The present invention also relates to the thermogel composition of 2-[(3-aminopropyl)amino]ethanethiol as mentioned above, for its use for treating radiation-induced cutaneous erythema.

The present invention also relates to the thermogel composition of 2-[(3-aminopropyl)amino]ethanethiol as mentioned above, for its use for treating or protecting mucosal or cutaneous tissue from damage associated with anticancer therapy, in particular with radiation and/or chemotherapeutic treatment of cancers.

The present invention also concerns a method of treating or protecting mucosal or cutaneous tissue from damage associated with anticancer therapy, in particular with radiation and/or chemotherapeutic treatment of cancers, by the application of the thermogel composition as defined above.

As damages associated with radiation treatment of cancers, the followings could be cited: oral mucositis (in case of radiation of head and neck cancer), epithelitis in the neck (in case of radiation of head and neck cancer), esophagitis (in case of radiation of the lung), cutaneous erythema (in case of radiation of breast), enteritis (in case of abdominal irradiation), vaginitis and vaginal dryness (in case of pelvic irradiation), rectitis (in case of pelvic irradiation), and loss of hair (in case of brain irradiation).

Especially, the present invention relates to the thermogel composition of 2-[(3-aminopropyl)amino]ethanethiol as mentioned above, for its use for treating the damages chosen from the group consisting of: epithelitis in the neck, cutaneous erythema in the breast cancer, and alopecia in case of brain irradiation.

EXAMPLES

A-Conversion of Amifostine into Aminothiol in Solution

Example A-1: In Hydrochloric Acid or Phosphoric Acid 1M Condition

A solution of amifostine (drug substance purchased from Shangai Boylechem Co., Ltd) at 350 mg/ml is prepared in hydrochloric acid or phosphoric acid 1M, and heated in a water-bath at 50° C. during 24 hours. After 24 hours, the composition of the solution was analyzed by HPLC method. The area percentages (%) of amifostine, aminothiol and disulfides are given in table below.

| Acid (1M) | % Amifostine | % Aminothiol | % Disulfides | % Others impurities |
|---|---|---|---|---|
| hydrochloric acid | 2.3% | 96.0% | 1.7% | 0.0% |
| phosphoric acid | 0.0% | 98.2% | 1.8% | 0.0% |

The conversion of amifostine in phosphoric acid 1M condition is complete (and almost complete in hydrochloric acid 1M with few residual amifostine) without formation of unknown impurity and only few disulfides.

Example A-2: In Hydrochloric Acid 4M Condition

A solution of amifostine at 500 mg/ml is prepared in hydrochloric acid 4M, and heated in a water-bath at 50° C. or at 60° C. during 24 hours. At 1 h-3 h-6 h and 24 hours, the composition of the solution was analyzed by HPLC method. The area percentages (%) of amifostine, aminothiol and disulfides are given in table below.

| Amifostine at 500 mg/ml HCl 4M | | 50° C. | 60° C. |
|---|---|---|---|
| 1 h | % Amifostine | — | 0.0 |
|  | % Aminothiol | — | 99.7 |
|  | % Disulfides | — | 0.3 |
| 3 h | % Amifostine | 2.9 | 0.0 |
|  | % Aminothiol | 96.7 | 99.6 |
|  | % Disulfides | 0.3 | 0.4 |
| 6 h | % Amifostine | 0.0 | 0.0 |
|  | % Aminothiol | 99.6 | 99.5 |
|  | % Disulfides | 0.4 | 0.5 |
| 24 h | % Amifostine | 0.0 | 0.0 |
|  | % Aminothiol | 99.0 | 99.1 |
|  | % Disulfides | 1.0 | 0.9 |

The conversion of amifostine in hydrochloric acid 4M condition is complete after 6 hours at 50° C. and only 1 hour at 60° C., without creating unknowing impurities.

Example A-3 (Comparative): In Citric Acid Condition

A solution of amifostine at 350 mg/ml is prepared in citric acid 1M (weak acid), and heated in a water-bath at 50° C. during 24 hours. After 24 hours, the composition of the solution was analyzed by HPLC method. The area percentages (%) of amifostine, aminothiol and disulfides (WR-33278) are given in table below.

| % Amifostine | % Aminothiol | % Disulfides | % Others impurities |
|---|---|---|---|
| 0.0% | 65.1% | 1.3% | 33.6% |

The conversion of amifostine in citric acid condition is complete, but not suitable due to formation of new unknowing impurities in large quantity.

This comparative example shows that the use of citric acid which is not a strong acid according to the invention is not suitable for the conversion of amifostine into aminothiol.

Example A-4 (Comparative): In Acetic Acid Condition

A solution of amifostine at 350 mg/ml is prepared in acetic acid 1M, and heated in a water-bath at 50° C. during 24 hours. After 24 hours, the composition of the solution was analyzed by HPLC method. The area percentages (%) of amifostine, aminothiol and disulfides are given in table below.

| % Amifostine | % Aminothiol | % Disulfides | % Others impurities |
|---|---|---|---|
| 3.1% | 79.3% | 1.1% | 16.4% |

The conversion of amifostine in acetic acid condition is not complete, it remains unconverted residual amifostine. Moreover, new unknowing impurities in large quantity are formed.

This comparative example shows that the use of acetic acid which is not a strong acid according to the invention is not suitable for the conversion of amifostine into aminothiol.

B-Example of Freeze-Drying Conditions

Example B-1: Freeze-Drying Using Hydrochloric Acid 1M as Matrix

A solution of amifostine is firstly converted into aminothiol in hydrochloric acid 1M, based on Example A-1. After conversion, the solution is diluted in water to obtain a final solution at 50 mg/ml expressed in aminothiol, and 2 ml are distributed in glass vial for lyophilization.

Example of Freeze-Dry Recipe

| Step | Temperature | Time | Pressure |
|---|---|---|---|
| Shelf load | 5° C. | 300 min | — |
| Freezing | Rate −60° C. | 40 min | — |
|  | Hold −60° C. | 360 min | — |
| Primary Drying | Hold −60° C. | 30 min | 600 μbar |
|  | Rate −50° C. | 60 min | 200 μbar |
|  | Hold −50° C. | 600 min | 200 μbar |
|  | Rate −40° C. | 60 min | 200 μbar |
|  | Hold −40° C. | 600 min | 200 μbar |
|  | Rate −10° C. | 120 min | 200 μbar |
|  | Hold −10° C. | 600 min | 200 μbar |
| Secondary Drying | Hold +20° C. | 240 min | 30 μbar |
| Storage | Hold +5° C. | — | 900 μbar |

After freeze-drying, the appearance of cake obtained is good. For the reconstitution, add 2 ml of placebo gel containing Poloxamer 407/188 19/6 w/w, to obtain a final thermosensitive gel of aminothiol at 50 mg/ml, with a gelling temperature between 25° C. and 30° C.

Example B-2: Freeze-Drying Using Hydrochloric Acid 4M and Poloxamers 21/4 as Matrix A solution of amifostine at 500 mg/ml is firstly converted totally into aminothiol in hydrochloric acid 4M during 1 hour at 60° C. (based on Example A-2). After conversion, the solution is diluted into Poloxamers P407/P188 21/4 w/w to obtain a final gel at 50 mg/ml expressed in aminothiol. Then 2 ml are distributed in glass vial for lyophilization.

Example of Freeze-Dry Recipe

| Step | Temperature | Time | Pressure |
|---|---|---|---|
| Shelf load | 5° C. | 600 min | — |
| Freezing | Rate −60° C. | 40 min | — |
|  | Hold −60° C. | 360 min | — |
| Primary Drying | Hold −60° C. | 30 min | 600 μbar |
|  | Rate −40° C. | 90 min | 200 μbar |
|  | Hold −40° C. | 600 min | 200 μbar |
|  | Rate −10° C. | 120 min | 200 μbar |
|  | Hold −10° C. | 600 min | 200 μbar |
| Secondary Drying | Hold +20° C. | 240 min | 30 μbar |
| Storage | Hold +5° C. | — | 900 μbar |

After freeze-drying, the cake obtained have good appearance.

For the reconstitution, add 1.4 ml of water, to obtain a final thermosensitive gel of WR-1065 at 50 mg/ml, with a gelling temperature between 28° C. and 30° C.

Example B-3: Freeze-Drying Using Hydrochloric Acid 4M and Poloxamers 18/6 as Matrix A solution of amifostine at 500 mg/ml is firstly converted totally into aminothiol in hydrochloric acid 4M during 1 hour at 60° C. (based on Example A-2). After conversion, the solution is diluted into Poloxamers P407/P188 18/6 w/w to obtain a final gel at 50 mg/ml expressed in aminothiol. Then 2 ml are distributed in glass vial for lyophilization.

The freeze-dry recipe applied is the same as presented in above Example B-2.

After freeze-drying, the cake obtained have good appearance.

For the reconstitution, add 1.4 ml of water, to obtain a final thermosensitive gel of aminothiol at 50 mg/ml, with a gelling temperature between 65° C. and 70° C.

Example B-4: Freeze-Drying Using Hydrochloric Acid 1M and Poloxamers 20/4 as Matrix A solution of amifostine at 350 mg/ml is firstly converted totally into aminothiol in hydrochloric acid 1M during 6 hours at 60° C. After conversion, the solution is diluted into Poloxamers P407/P188 20/4 w/w to obtain a final gel at 50 mg/ml expressed in aminothiol. Then 2 ml are distributed in glass vial for lyophilization.

The freeze-dry recipe applied is the same as presented above in Example B-2.

After freeze-drying, the cake obtained have good appearance.

For the reconstitution, add 1.5 ml of water, to obtain a final thermo sensible gel of WR-1065 at 50 mg/ml, with a gelling temperature between 30° C. and 35° C.

Example B-5: Freeze-Drying Using Hydrochloric Acid 1M and Polysorbate 80 as Matrix A solution of amifostine is firstly converted into aminothiol in hydrochloric acid 1M, based on Example A-1. After conversion, the solution is diluted in water containing 0.2% of Polysorbate 80 as cryoprotectant, to obtain a final solution at 50 mg/ml expressed in aminothiol. 2 ml are distributed in glass vial for lyophilization.

The freeze-dry recipe applied is the same as presented above in Example B-2.

During freeze-drying, the cake obtained have collapsed giving a melted aspect to the cake. For the reconstitution, add 2 ml of placebo gel containing Poloxamer 407/188 19/6 w/w, to obtain a final thermosensitive gel of aminothiol at 50 mg/ml, with a gelling temperature between 25° C. and 30° C.

Example B-6: Freeze-Drying Using Hydrochloric Acid 4M as Matrix

A solution of amifostine is firstly converted totally into aminothiol in hydrochloric acid 4M, based on Example A-2. After conversion, the solution is diluted in water to obtain a final solution at 50 mg/ml expressed in aminothiol, and 2 ml are distributed in glass vial for lyophilization.

Example of Freeze-Dry Recipe

| Step | Temperature | Time | Pressure |
|---|---|---|---|
| Shelf load | 5° C. | 120 min | — |
| Freezing | Rate −55° C. | 120 min | — |
|  | Hold −55° C. | 720 min | — |
| Primary Drying | Hold −55° C. | 30 min | 200 µbar |
|  | Rate −40° C. | 90 min | 200 µbar |
|  | Hold −40° C. | 180 min | 200 µbar |
|  | Rate −30° C. | 60 min | 200 µbar |
|  | Hold −30° C. | 300 min | 200 µbar |
|  | Rate +5° C. | 180 min | 200 µbar |
|  | Hold +5° C. | 360 min | 200 µbar |
| Secondary Drying | Hold +20° C. | 240 min | 30 µbar |
| Storage | Hold +5° C. | — | 900 µbar |

During freeze-drying, the cake obtained have collapsed giving a melted aspect to the cake.

For the reconstitution, add 2 ml of placebo gel containing Poloxamer 407/188 19/6 w/w, to obtain a final thermosensitive gel of aminothiol at 50 mg/ml, with a gelling temperature around 30° C.

Example B-7: Freeze-Drying Using Hydrochloric Acid 4M and Hydroxide Sodium as Matrix A solution of amifostine is firstly converted totally into aminothiol in hydrochloric acid 4M, based on Example A-2. After conversion, the pH of solution is adjusted to pH>6.0 adding hydroxide sodium 10M. Then, the solution adjusted is diluted in water to obtain a final solution at 50 mg/ml expressed in aminothiol. 2 ml are distributed in glass vial for lyophilization.

The freeze-dry recipe applied is the same as presented above in Example B-1.

During freeze-drying, the cake obtained have considerably collapsed giving a melted appearance to the cake. For the reconstitution, add 2 ml of placebo gel containing Poloxamer 407/188 19/6 w/w, to obtain a final thermosensitive gel of aminothiol at 50 mg/ml, with a gelling temperature around 30° C.

C-Preparation of Gels of Aminothiol

Example C-1: Reconstitution of Freeze-Dried Powder with Poloxamers Gel to Obtain a Gel of Aminothiol at 50 mg/ml In order to prepare a gel of aminothiol at 50 mg/ml, add 2 ml of P407/P188 19/6 w/w to the freeze-dried obtained as described on Example B-1 (HCl 1M in lyophilization matrix) or Example B-5 (HCl 1M+PS80 in lyophilization matrix). The final gel formulated has a gelling temperature between 25-30° C.

Example C-2: Reconstitution of Freeze-Dried Powder with Poloxamers Gel to Obtain a Gel of Aminothiol at 50 mg/ml In order to prepare a gel of aminothiol at 50 mg/ml, add 2 ml of P407/P188 19/6 w/w to the freeze-dried obtained as described on Example B-6 (HCl 4M in lyophilization matrix) or Example B-7 (HCl 4M+NaOH in lyophilization matrix). The final gel formulated has a gelling temperature around 30° C.

Example C-3: Reconstitution of Freeze-Dried Powder with Aqueous Solution to Obtain a Gel of Aminothiol at 50 mg/ml In order to prepare a gel of aminothiol at 50 mg/ml, add 1.4 ml of solution containing for example mint flavour/bitter masker/water 4%/0.05%/95.95% w/w/w to the freeze-dried powder obtained as described on Example B-2. The final gel formulated has a gelling temperature around 27-29° C.

Example C-4: Reconstitution of Freeze-Dried Powder with Aqueous Solution to Obtain a Gel of Aminothiol at 50 mg/ml In order to prepare a gel of aminothiol at 50 mg/ml, add 1.5 ml of water to the freeze-dried powder obtained as described on Example B-4. The final gel formulated has a gelling temperature around 30-35° C.

Example C-5: Reconstitution of Freeze-Dried Powder with Aqueous Solution to Obtain a Gel of Aminothiol at 50 mg/ml In order to prepare a gel of aminothiol at 50 mg/ml, add 1.4 ml of water to the freeze-dried powder obtained as described on Example B-3. The final gel formulated has a gelling temperature around 65-70° C.

D-Stability of Lyophilized Powder of Aminothiol (WR-1065)

A stability study is performed to compare stability of:
WR-1065 obtained by conversion of amifostine (350 mg/ml or 500 mg/ml) in acidic condition (respectively HCl 1M or HCl 4M), diluted in water or in P407/P188 mixture and then lyophilized (based on examples described in parts A & B), and
WR-1065 hydrochloride salt crystalline powder.

Stability is assessed by analysis of samples stored under argon atmosphere at 25° C./60% RH. The aim of argon is to provide two materials under same stability condition.

|  |  | Amifostine | Aminothiol | Disulfides | Unknow |
|---|---|---|---|---|---|
| WR-1065·2HCl native under argon atm. | T0 | 0.0 | 99.7 | 0.3 | <LOQ |
|  | T15d-25° C./60% RH | 0.0 | 99.6 | 0.4 | <LOQ |
|  | T1m-25° C./60% RH | 0.0 | 99.3 | 0.5 | 0.2 |
| Freeze-dried (350 mg/ml amifostine conversion in HCl 1M, diluted in water) under argon atm. | T0 | 3.8 | 94.6 | 1.6 | ND |
|  | T15d-25° C./60% RH | 3.4 | 95.5 | 1.1 | <LOQ |
|  | T1m-25° C./60% RH | 3.1 | 95.8 | 1.1 | ND |
| Freeze-dried (500 mg/ml amifostine conversion in HCl 4M, diluted in P407/P188) under argon atm | T0 | 0.0 | 99.1 | 0.9 | ND |
|  | T15d-25° C./60% RH | 0.2 | 99.2 | 0.6 | <LOQ |
|  | T1m-25° C./60% RH | 0.0 | 98.9 | 0.6 | 0.5 |

According to the stability results obtained:
after 1 month at 25° C./60% RH, less than 2% of impurities have been detected in all tested aminothiol formulations and this value remained stable; and
freeze-dried WR-1065 obtained from amifostine conversion in acidic conditions and WR-1065 hydrochloride salt have the same stability.

E-Attempts to Develop Stable Amifostine Active Metabolite Gel Treatment

Example E-1: Stabilization of Aminothiol

Initially, the possibility to develop a thermogel of aminothiol was evaluated, to obtain a stable ready-to-use formulation with at least 6 months stability in refrigerated conditions.

Aminothiol gel formulations are not stable when stored at 5° C. or at room temperature. During storage, aminothiol degrades in oxidation impurity (disulfide WR-33278) significantly.

For example, an aminothiol gel at 50 mg/ml presented an increase of disulfide impurity from 3.6 to 13.8% (area %) after 15 days storage at 5° C.

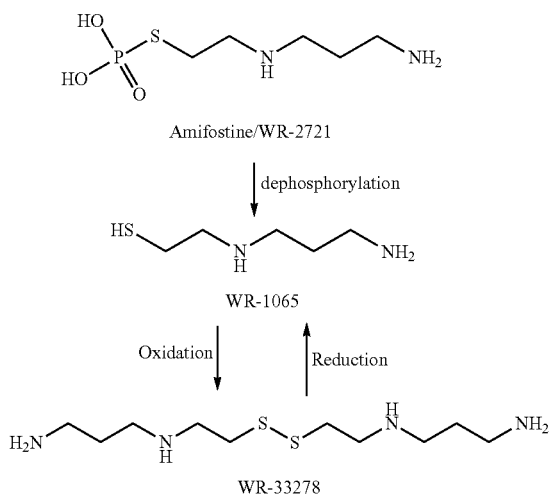

Amifostine/WR-2721

↓ dephosphorylation

WR-1065

Oxidation ↓ ↑ Reduction

WR-33278

Different parameters were tested to improve aminothiol stability in solution:
additives of preservative agent like an antioxidant and/or chelating agent (metabisulfide, EDTA, tartaric acid, citric acid, N-acetylcysteine, alpha lipoïc acid, hydrochloric cysteine, ascorbic acid, Dithiothreitol DTT),
nitrogen inerting, or
drug concentration (50 mg/ml, 220 mg/ml).

For example, a stability study was performed after one month at 5° C.±3° C. on aminothiol gel at 50 mg/ml. Firstly, aminothiol solution is prepared by conversion of 350 mg/ml amifostine solution heated in HCl 1M (based on example A-1). Then the solution is diluted at 50 mg/ml (expressed in aminothiol) in different antioxidant solution and put at 5° C.±3° C. stability.

|  | Antioxidant reagent | Time | Amifostine | Aminothiol | Disulfides + Unknown |
|---|---|---|---|---|---|
| 1 | None | Initial | 2.2% | 96.2% | 1.6% |
|  |  | 7 days | 2.2% | 92.4% | 5.4% |
|  |  | 1 month | 2.0% | 84.2% | 13.8% |
| 2 | Tartaric acid 0.5% | Initial | 2.3% | 96.6% | 1.1% |
|  |  | 7 days | 2.2% | 93.2% | 4.6% |
|  |  | 1 month | 1.8% | 84.7% | 13.5% |
| 3 | Citric acid 0.5% | Initial | 2.3% | 96.5% | 1.1% |
|  |  | 7 days | 2.2% | 93.2% | 4.6% |
|  |  | 1 month | 1.8% | 85.0% | 13.2% |
| 4 | N-acetylcysteine 1.6% | Initial | 2.0% | 83.9% | 14.1% |
|  |  | 7 days | 1.5% | 69.3% | 29.2% |
|  |  | 1 month | 0.9% | 39.8% | 59.3% |
| 5 | α-Lipoic acid 0.04% | Initial | 2.3% | 92.4% | 5.3% |
|  |  | 7 days | 2.1% | 93.1% | 4.8% |
|  |  | 1 month | 2.0% | 83.6% | 14.4% |
| 6 | Cysteine hydrochloride 0.5% | Initial | 2.3% | 96.2% | 1.5% |
|  |  | 7 days | 2.1% | 93.2% | 4.7% |
|  |  | 1 month | 1.9% | 79.6% | 18.5% |
| 7 | Ascorbic acid 0.5% | Initial | 2.3% | 94.1% | 3.7% |
|  |  | 7 days | 2.1% | 85.6% | 12.2% |
|  |  | 1 month | 1.9% | 76.9% | 21.2% |
| 8 | DTT 0.05% | Initial | 2.3% | 96.7% | 1.1% |
|  |  | 7 days | 2.2% | 94.5% | 3.3% |
|  |  | 1 month | 2.0% | 83.4% | 14.6% |
| 9 | DTT 0.5% | Initial | 2.3% | 97.0% | 0.7% |
|  |  | 7 days | 2.2% | 95.5% | 2.3% |
|  |  | 1 month | 2.0% | 97.5% | 0.5% |

Whatever the additives tested (antioxidant, chelating agent), aminothiol solution is not stable enough at 5° C., and the disulfide bridge formation is not prevented. Moreover, N-acetylcysteine accelerates the degradation of aminothiol, creating an important new impurity. So, this option of aminothiol stabilization is not suitable.

Among them, the best stability was obtained by the formulation with DTT at 0.5%. It is stable for at least one month at 5° C., but the amount of DTT at 0.5% is not appropriate for intended use.

Example E-2: Rapid Conversion from Amifostine into Aminothiol

As aminothiol is not stable, the inventors evaluated the possibility to develop a thermogel of amifostine which will be converted into aminothiol (WR-1065) just before administration. To develop a commercially suitable product, the aim is to find suitable conditions to obtain total conversion (>90%) in less than 30 minutes.

In the following experiments, amifostine crystalline powder was added to different placebo gels, and conversion rate and yield into Aminothiol WR-1065 was measured.

Different parameters were tested:
- acid (hydrochloric acid, acetic acid, phosphoric acid, citric acid, sulfuric acid, perchloric acid),
- amifostine concentration (20-80 mg/ml), or
- temperature (37° C. or room temperature).

For example, amifostine crystalline powder was directly incorporated at a concentration of 40 mg/ml in placebo gels containing a mixture of 14% w/w of Poloxamer P407 and 26% w/w of P188 and 15% or 30% v/v of HCl 1M. Conversion was monitored after 30 min at 37° C. and from 30 min up to 3 hours at room temperature.

| % HCl | Condition | Amifostine | Aminothiol | Disulfide | Unknown |
|---|---|---|---|---|---|
| HCl 30% | RT/T = 0 | 98.9% | 1.1% | 0.0% | 0.0% |
| | RT/T = 35 min | 94.2% | 5.3% | 0.3% | 0.2% |
| | RT/T = 70 min | 89.9% | 9.3% | 0.4% | 0.3% |
| | RT/T = 3 H | 73.1% | 25.3% | 0.9% | 0.7% |
| | 37° C./T = 0 | 99.1% | 0.8% | 0.1% | 0.1% |
| | 37° C./T = 35 min | 68.7% | 30.0% | 0.7% | 0.6% |
| HCl 15% | RT/T = 0 | 96.9% | 1.4% | 1.1% | 0.6% |
| | RT/T = 35 min | 93.5% | 3.7% | 1.8% | 0.9% |
| | RT/T = 70 min | 87.3% | 9.2% | 2.4% | 1.1% |
| | RT/T = 3 H | 71.1% | 25.1% | 2.6% | 1.2% |
| | 37° C./T = 0 | 98.4% | 1.2% | 0.2% | 0.2% |
| | 37° C./T = 35 min | 63.1% | 33.6% | 2.2% | 1.1% |

After 30 min at room temperature or at 37° C., the conversion into aminothiol is very low, whatever the parameters tested (the maximum obtained is ≈30%).

Example E-3: Rapid Conversion from Disulfide into Aminothiol

As the conversion of amifostine into aminothiol within 30 minutes is difficult, another option of formulation was evaluated, converting disulfide WR-33278 into aminothiol WR-1065 just before administration.

Conversion of disulfide to aminothiol was tested on a gel formulation containing high disulfide amount (37.7% area). To reduce disulfide bonds, a strong reducing agent, dithiothreitol (DTT), was tested at different concentrations Firstly, aminothiol solution is prepared by conversion of 350 mg/ml amifostine solution heated in HCl 1M (based on example A-1). Then the solution is diluted at 50 mg/ml (expressed in aminothiol) in water and stored for a few days at room temperature to obtain high formation of disulfides by degradation. After a few days, DTT is finally added to the gel and analyses were performed after 30 minutes of incubation with DTT at room temperature.

| Purity profile 30 min after addition of DTT | | | | | |
|---|---|---|---|---|---|
| | | % Area | | | |
| | RRT | without DTT | 5 mM DTT | 41 mM DTT | 81 mM DTT |
| Amifostine | 1 | 5.6 | 5.0 | 6.2 | 7.0 |
| Aminothiol | 3.6 | 56.8 | 50.7 | 93.4 | 90.5 |
| Disulfide | 3.7 | 37.7 | 44.3 | 0.4 | 2.6 |

Using DTT, disulfides can be reduced considerably to aminothiol in 30 minutes at room temperature, but the concentration needed in DTT is higher than the amount authorized for toxicology reactions.

F-Preclinical Evaluation of a Thermogel According to the Invention Containing Aminothiol for the Prevention of Radiation-Related Oral Mucositis

Example F-1: Preparation of Gel Formulations for Efficacy Study

The following formulations were used for an efficacy study as explained hereafter. Formulations were prepared the day before the efficacy study, stored at 5° C. and analyzed on dosing day.

Purity of amifostine batch used was taken into account. For aminothiol formulation, the concentration in mg/ml is expressed as equivalent amifostine concentration. Using molecular ratio, 80 mg/ml amifostine is equivalent to 50 mg/ml aminothiol.

All gel formulations were colored by brilliant blue for a better visualization of the application.

| Formulation | Preparation method | Final composition % w/w |
|---|---|---|
| Gel n°1 aminothiol | Prepared by mixing 22.9% v/v of a 350 mg/ml concentrated solution of amifostine previously converted into thiol (heating 24 h at 50° C. in 15% Kleptose HPB in HCl 1M) with 77.1% v/v of a placebo gel | Amifostine 80 mg/ml converted in thiol (50 mg/ml) Kleptose HPB 3.4% HCl 1M 19.5% Kolliphor P407 11.6% Kolliphor P188 20.8% Water milliQ 44.7% |
| Gel n°2 amifostine | Prepared by mixing amifostine powder with a placebo gel alkalinized with NaOH. | Amifostine 80 mg/ml Kleptose HPB 10% NaOH 1M 25% Kolliphor P407 11.5% Kolliphor P188 20% Water milliQ 33.5% |
| Gel n°3 placebo | Placebo gel preparation | Kolliphor P407 15% Kolliphor P188 27% Water milliQ 58% |
| Solution IV | Prepared by mixing amifostine in NaCl 0.9% | Amifostine 20 mg/ml in NaCl 0.9% |

Gel n°1 has the same composition as a thermogel composition according to the invention (corresponding to a reconstituted lyophilisate according to the invention).

Example F-2: Efficacy Study of the Gel Formulations of Example F-1

The aim of this example was to evaluate the efficacy of the thermogel compositions of example F-1 containing amifostine against radiation-induced oral mucositis in vivo.

Female C57BL/6 mice (12 weeks old) purchased from Janvier CERT (Le Genest St. Isle, France) were used after an acclimation time of 7 days. They had free access to food (SAFE reference R0340, Augy, France) and water. They were housed on a 12 hours light/dark cycle at a room temperature of 22° C.±2° C. and a relative humidity of 55%±15%.

Irradiation was carried out locally with a X-ray Varian NDI 226 tube (200 kV, 15 mA, 0.2 mm Cu) at a dose rate of 1.33 Gy/min, the rest of the body being protected by a lead shield. Mice were euthanized when body weight loss exceeded 20% of the initial weight for more than 24 hours or in case of severe clinical signs (ethical endpoints).

The following experiment was carried out by using the model of oral mucositis as described in Mangoni, M., Vozenin, M. C., Biti, G., and Deutsch, E. (2012). Normal tissues toxicities triggered by combined anti-angiogenic and radiation therapies: hurdles might be ahead. British journal of cancer, 107, 308-314.

Two parameters were monitored: the body weight and the Parkins score. This represents an arbitrary score system devised by Parkins and co-workers with separate scores for edema and erythema evaluated by macroscopic observation (Parkins, C. S., Fowler, J. F., and Yu, S. (1983). A murine model of lip epidermal/mucosal reactions to X-irradiation. Radiotherapy and oncology: Journal of the European Society for Therapeutic Radiology and Oncology 1, 159-165). Indeed, at high doses of irradiation, lip epidermal/mucosal reactions are observed, beginning approximately 5 days after irradiation and reaching a peak about 10 to 13 days after irradiation. They consist mainly of an edema and an erythema. The Parkins score represents the sum of the score for edema and the score for erythema.

The Parkins score is calculated as follows: "Parkins score"=edema score+erythema score.

|  | Erythema or exudation score |
|---|---|
| 50-50 doubtful if any abnormally pink | 0.5 |
| Slight but definite redding | 1 |
| Severe redding | 2 |
| Focal desquamation | 3 |
| Exudate or crusting involving about half lip area | 4 |
| Exudate or crusting involving more than half lip area | 5 |

|  | Edema score |
|---|---|
| 50-50 doubtful if any swelling | 0.5 |
| Slight but definite swelling | 1 |
| Severe swelling | 2 |

Experiment

A single dose irradiation was delivered to the snout of mice. This induced a mucosal/epidermal lip reaction that was monitored through macroscopic observation and scoring.

A blind experiment was conducted to determine the effect of gels containing or not an active substance on the severity and duration of oral mucositis. Three gels were evaluated: a placebo gel (Gel n°3), a gel containing 80 mg/ml Amifostine (Gel n°2) and a gel containing 50 mg/ml Amifostine thiol (Gel n°1) (corresponding to 80 mg/ml Amifostine). Mice were anesthetized (intraperitoneal injection of Ketamine 75 mg/kg+Domitor 1 mg/kg) 10 minutes before gel application. The gel was applied into the mouth (5 µl on each cheek) and onto the lips (40 µl). So, a total volume of 50 µl covered the mouse mucosa, which corresponds to 4 mg Amifostine per mouse. Mice snouts were irradiated 30 minutes after the application of the gel using a 20 Gy single fraction (dose rate 1.33 Gy/min). Antisedan was injected 1 hour after the injection of the anesthetic mix. These mice were compared with mice receiving an intravenous (IV) injection of Amifostine (4 mg per mouse, i.e. corresponding to an intravenous injection of 200 µl of a 20 mg/ml Amifostine solution) 30 minutes before irradiation and to a control group of mice receiving only a 20 Gy localized irradiation.

To sum up, 30 mice were allocated to 5 groups and then irradiated:
Control
Placebo gel
Amifostine gel (80 mg/ml, 4 mg amifostine/mouse)
Aminothiol gel (50 mg/ml, corresponding to 80 mg/ml amifostine or 4 mg amifostine/mouse)
Amifostine intravenous (IV) (20 mg/ml, 4 mg amifostine/mouse)

Graphs depicting the evolution of the Parkins score and the body weight over time are presented in FIG. 1. In FIG. 1, the curve (*) corresponds to the control, the curve (■) corresponds to the placebo gel, the curve (♦) corresponds to the amifostine gel, the curve (▲) corresponds to the amifostine thiol gel, and the curve (x) corresponds to the amifostine IV.

The irradiation of mice snout at a dose of 20 Gy in a ventral position induced a severe phenotype characterized by a significant body weight loss and a worsening of the general health status. All the control mice had to be sacrificed between day 14 and day 20. In the placebo gel group, mice exhibited a trend towards an even worse phenotype, as they had to be sacrificed a little bit earlier. The median survival was of 16 days versus 19 days for the placebo gel and the control groups respectively. However, it has to be noticed that the difference was not statistically significant (Log-rank test). Surprisingly, the presence of Amifostine in the gel had no visible impact on the development and the intensity of the mucositis, as mice presented a similar phenotype over time to those of the control group mice. On the contrary, the intravenous injection of Amifostine resulted in a mucosal reaction of moderate intensity. Edema and erythema completely disappeared as soon as day 20 after irradiation and no second peak (healing period) was observed for this group (FIG. 1). Interestingly, with the Amifostine thiol gel, mice showed an intermediate phenotype. They did not lose weight during the acute reaction (days 10 to 15), even if an established mucositis was detected. These mice did not reach an endpoint leading to their sacrifice and all the mice were still alive at the end of the experiment, in clear contrast to the fate of mice of the Amifostine gel group.

The opposite phenotype observed for the Amifostine gel and the Amifostine thiol gel groups and the clear absence of efficacy of the Amifostine gel suggest that Amifostine is not or not efficiently converted into Amifostine thiol when it is included in the gel and applied at the snout. Thus, the free active compound amifostine thiol has to be delivered directly to prevent at least partly the development of the radiation-induced mucositis.

Example F-3: Preparation of Gel Formulations for a Second Efficacy Study

The following formulations were used for an efficacy study as explained hereafter. Formulations were prepared the day before the efficacy study, stored at 5° C. and analyzed on dosing day.

Purity of amifostine batch used was taken into account and concentration in mg/ml is expressed as equivalent amifostine concentration.

| Formulation | Preparation method | Final composition % w/w |
|---|---|---|
| Gel n°4 aminothiol at 12.5 mg/ml | Prepared by mixing 8% v/v of a 250 mg/mL concentrated solution of amifostine previously converted to thiol (heating 25 h at 50° C. in 15% Kleptose HPB in HCl 1M) with 92% v/v of a placebo gel | Amifostine 20 mg/ml converted in thiol (12.5 mg/ml) Kleptose HPB 1.2% HCl 1M 6.8% Kolliphor P407 13.8% Kolliphor P188 24.8% Water milliQ 53.4% |
| Gel n°5 aminothiol at 25 mg/ml | Prepared by mixing 11.4% v/v of a 350 mg/ml concentrated solution of amifostine previously converted to thiol (heating 25 h at 50° C. in 15% Kleptose HPB in HCl 1M) with 88.6% v/v of a placebo gel | Amifostine 40 mg/ml converted in thiol (25 mg/ml) Kleptose HPB 1.7% HCl 1M 9.7% Kolliphor P407 13.8% Kolliphor P188 24.8% Water milliQ 53.4% |
| Gel n°6 aminothiol at 50 mg/ml | Prepared by mixing 22.9% v/v of a 350 mg/ml concentrated solution of amifostine previously converted to thiol (heating 25 h at 50° C. in 15% Kleptose HPB in HCl 1M) with 77.1% v/v of a placebo gel | Amifostine 80 mg/ml converted in thiol (50 mg/ml) Kleptose HPB 3.4% HCl 1M 19.5% Kolliphor P407 11.6% Kolliphor P188 20.8% Water milliQ 44.7% |
| Gel n°7 Placebo | Placebo gel preparation | Kolliphor P407 14.5% Kolliphor P188 26.2% Kleptose HPB 0.4% Water milliQ 58.9% |
| Solution IV | Prepared by mixing amifostine in NaCl 0.9% | Amifostine 20 mg/ml in NaCl 0.9% |

Gels n°4, 5, and 6 have the same composition as a thermogel composition according to the invention (corresponding to a reconstituted lyophilisate according to the invention).

Example F-4: Efficacy Study of the Gel Formulations of Example F-3

The purpose of this second efficacy experiment was to confirm the results obtained in the first experiment regarding the impact of Amifostine thiol on radiation-induced mucositis and to establish data about a dose-response relationship. As an intermediate effect was observed with the gel containing 80 mg/ml Amifostine (corresponding to 50 mg/ml amifostine thiol), it would have been interesting to test a more concentrated gel to determine if we could improve more radically oral mucosa protection against ionizing radiation.

The experiment was conducted with gels containing 20, 40 or 80 mg/ml Amifostine (corresponding to 12.5, 25 or 50 mg/ml amifostine thiol respectively). A lower dose of irradiation (a single fraction irradiation of 18 Gy) was delivered to the snout, so that all the mice could be kept alive until the end of the experiment. Different amounts of compound were administered to mice (1; 2 or 4 mg per mouse).

The same experimental procedure as for in example F-2 was used. Briefly, mice were anesthetized, Amifostine or Amifostine thiol was delivered 10 minutes later or not depending on the group (gel application or intravenous injection), mice were irradiated dorsally at an 18 Gy dose 30 minutes after the administration of Amifostine or Amifostine thiol and awakened 20 minutes later.

Forty mice were allocated to 6 groups:
Control (n=6 mice);
Placebo gel (n=6 mice);
Amifostine thiol 20 mg/ml gel (1 mg amifostine/mouse, n=6 mice);
Amifostine thiol 40 mg/ml gel (2 mg amifostine/mouse, n=6 mice);
Amifostine thiol 80 mg/ml gel (4 mg amifostine/mouse, n=6 mice); and
Amifostine intravenous (IV) (20 mg/ml) (4 mg amifostine/mouse, n=5 mice).

For each group, the development of oral mucositis was evaluated on 5 or 6 mice depending on the group. An 18 Gy dose irradiation induced a less severe phenotype than the 20 Gy dose irradiation that was used in the first efficacy experiment. The body weight loss was manageable and all the mice were still alive at the end of the experiment.

Figure 2:
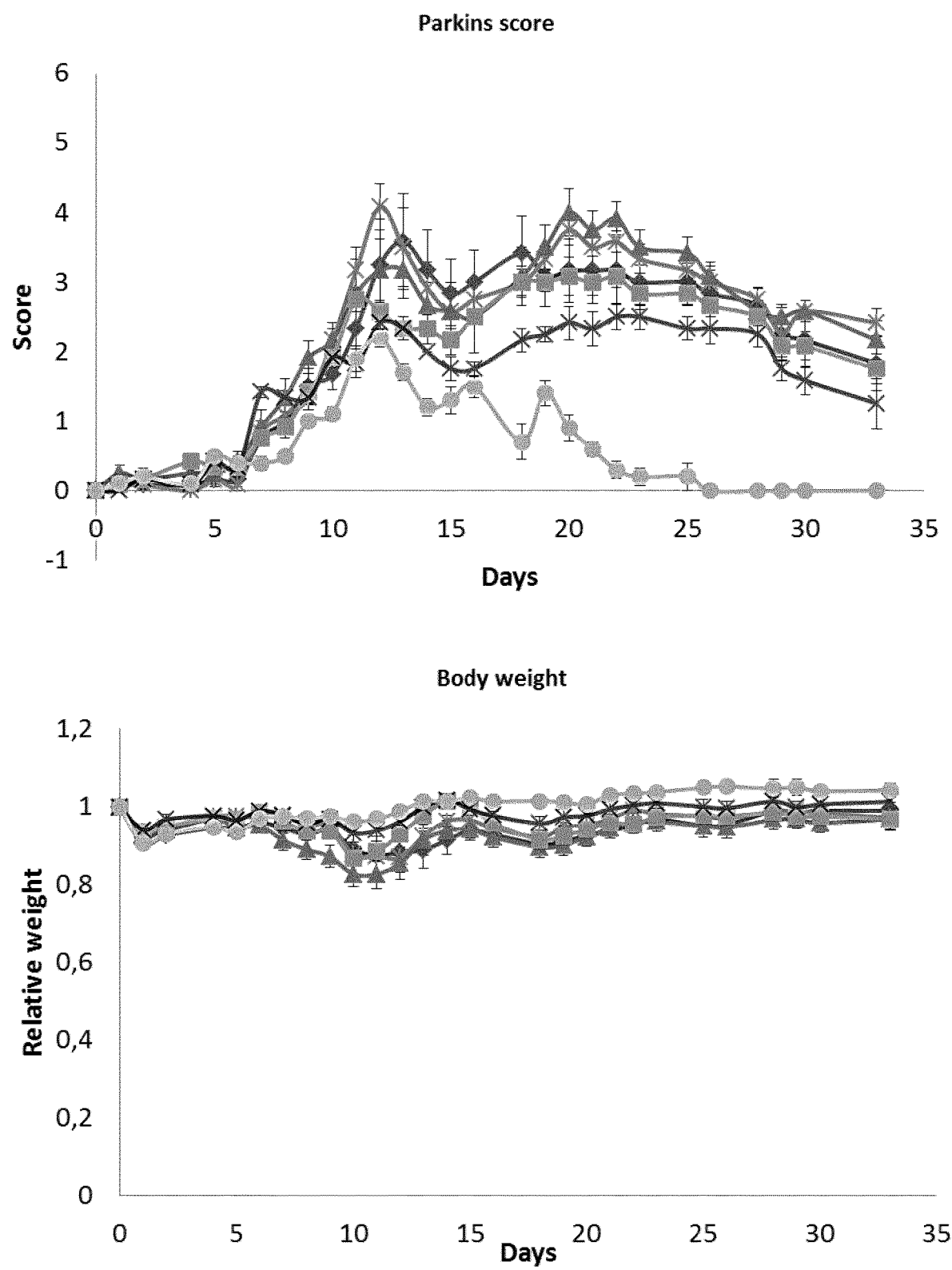

Graphs depicting the evolution of the Parkins score and the body weight over time are presented in FIG. 2. In FIG. 2, the curve (♦) corresponds to the control, the curve (*) corresponds to the placebo gel, the curve (▲) corresponds to the gel n°4, the curve (■) corresponds to the gel n°5, the curve (x) corresponds to the gel n°6, and the curve (●) corresponds to the amifostine IV.

As expected, the irradiation induced a peak of mucosal reaction in the control group at day 13, as shown in FIG. 2. This was followed by a healing period extending from day 18 to day 30 as already observed in example F-2 for the Amifostine thiol gel group. For the Amifostine IV group, the acute peak of mucosal reaction was also observed at day 12, but it was of lower intensity than what is observed for the control gel (score of 2.2 versus 3.6 respectively). The healing period was nearly absent in this group as it was already noticed in example F-2. For the other groups, the score at the peak was of 4.1; 3.2; 2.8 and 2.4 for the placebo gel and the 20 mg/ml; 40 mg/ml and 80 mg/ml Amifostine (corresponding to 12.5, 25 or 50 mg/ml amifostine thiol) gels respectively. During the healing period, the curves for the control, the placebo gel, the 20 mg/kg and the 40 mg/kg Amifostine thiol gels were barely distinguishable from one another. The application of the 20 mg/kg Amifostine thiol gel did not alter the intensity of the peak of mucositis and the score recorded during the healing period was comparable to those of the control group. With the 40 mg/ml Amifostine thiol gel, a decrease of the intensity of the mucositis peak was observed. This was further enhanced with the 80 mg/ml Amifostine thiol gel, which also induced a reduction of the score recorded during the healing period.

Example F-5: Preparation of Gel Formulations by Reconstitution of Freeze-Dried Powder with Aqueous Solution for a Third Efficacy Study The following formulations were used for an efficacy study with fractionated irradiation as explained hereafter. The freeze-dried thermogel were reconstituted the day before the efficacy study, stored at 5° C. and analyzed on dosing day.

Purity of amifostine batch used was taken into account and concentration in mg/ml is expressed as equivalent amifostine concentration.

| Formulation | Preparation method | Final composition % w/w |
|---|---|---|
| Gel n°8 Placebo | Prepare the Placebo gel Freeze-drying the placebo gel | Kolliphor P407: 21% Kolliphor P188: 4% |

-continued

| Formulation | Preparation method | Final composition % w/w |
|---|---|---|
| Gel | Reconstitute freeze-dried powder using water to volume | Water 75% |
| Gel n°9 aminothiol at 25 mg/ml | Prepare the gel by mixing 8% v/v of a 500 mg/ml concentrated solution of amifostine previously converted into thiol (heating 1 h at 60° C. in HCl 4M) with 92% v/v of a placebo gel (P407/P188: 20/4) Freeze-drying the gel Reconstitution freeze-dried powder using water to volume | Amifostine 40 mg/ml converted in thiol (25 mg/ml) HCl 4M: ~8% Kolliphor P407: 18.4% Kolliphor P188: 3.7% Water: ~69.9% |
| Solution IV | Prepared by mixing amifostine in NaCl 0.9% | Amifostine 20 mg/ml in NaCl 0.9% |

After reconstitution, final formulation Gels n°8 and 9 have the same composition as that before lyophilization, according to the invention.

Example F-6: Efficacy Study of the Gel Formulations of Example F-5

The purpose of this third efficacy experiment was to confirm the results obtained in the first experiment regarding the impact of Amifostine thiol on radiation-induced mucositis in a setting of a fractionated irradiation regimen and using reconstituted freeze-dried thermogels.

The experiment was conducted with a placebo gel and a gel containing 40 mg/ml Amifostine (corresponding to 25 mg/ml amifostine thiol). Four fractions of 8 Gy were delivered for four consecutive days (everyday from day 0 to day 3; day 0 corresponding to the first day of treatment) to the snout. The fractionation scheme of four fractions of 8 Gy was chosen, because it is biologically equivalent to 1 fraction of 18 Gy (Biologically Effective Dose: BED~120 Gy). The same amount of compound (corresponding to 2 mg amifostine per mouse) was administered to mice before each fraction of irradiation. Thus, the compound was applied 4 times for four consecutive days.

For each day, a similar experimental procedure as for in example F-2 was used. Briefly, mice were anesthetized, Amifostine or Amifostine thiol was delivered 10 minutes later or not depending on the group (gel application or intravenous injection), mice were irradiated dorsally at an 8 Gy dose 30 minutes after the administration of Amifostine or Amifostine thiol and awakened 20 minutes later. The same experimental procedure was repeated for 4 consecutive days.

Twenty-four mice were allocated to 4 groups:
Irradiation without gel (n=6 mice);
Irradiation with Amifostine thiol gel (25 mg/ml, corresponding to 2 mg amifostine or 1.25 mg amifostine thiol/mouse/day) (n=6 mice);
Irradiation with Placebo gel (n=4 mice);
Irradiation with intravenous injection (IV) of amifostine (2 mg amifostine/mice) (n=6 mice).

Figure 3:
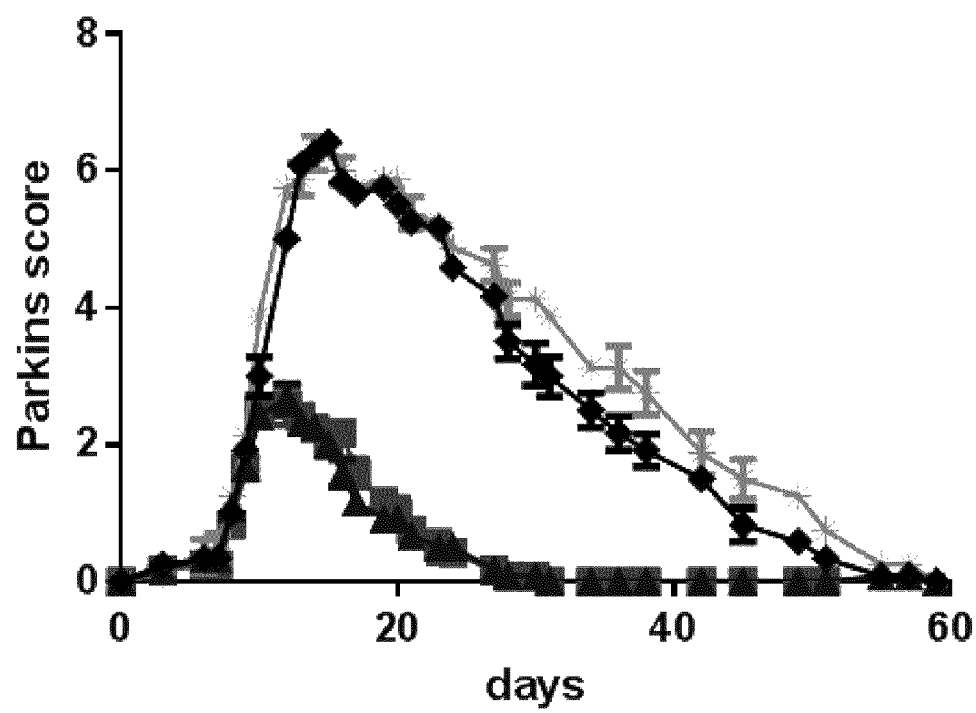
Figure 3:
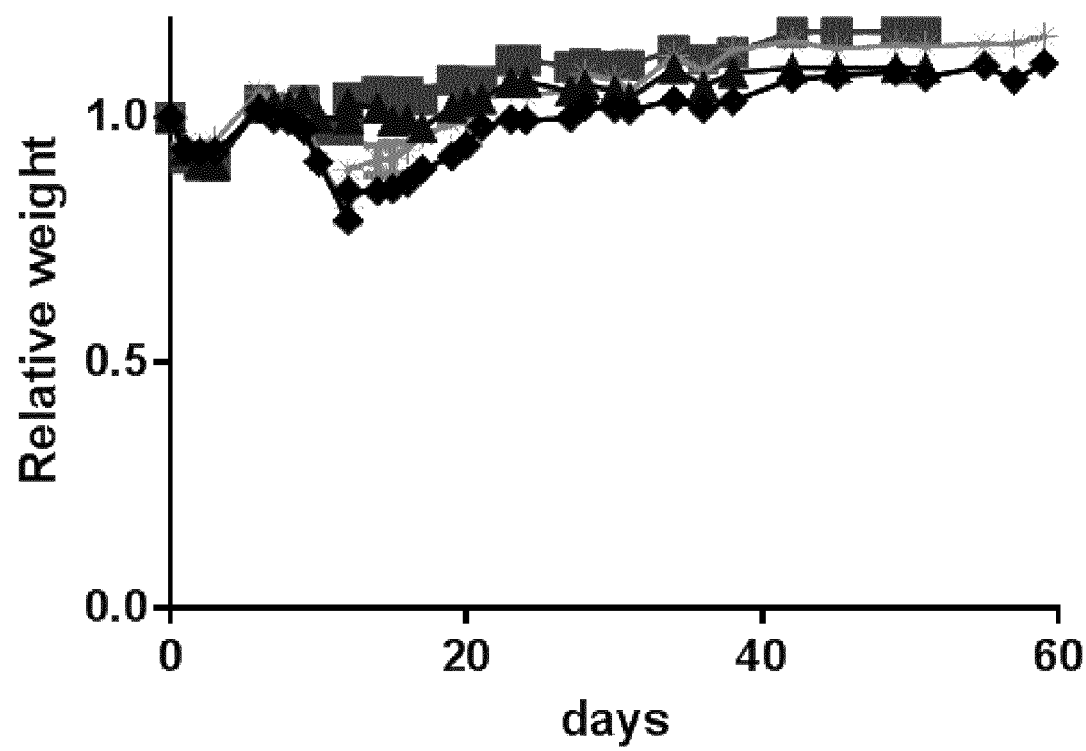

For each group, the development of oral mucositis and body weight were analyzed daily (6 days/week) from day 3 to day 60. Graphs depicting the evolution of the Parkins score and the body weight over time are presented in FIG. 3. In FIG. 3, the curve (◆) corresponds to the control, the curve (∗) corresponds to the placebo gel, the curve (▲) corresponds to the gel n°9, the curve (■) corresponds to the amifostine IV.

As already observed after a single fraction irradiation, a peak of mucosal reaction was induced 15 days after the first fraction of irradiation in the control group. The healing period extended until 60 days after irradiation. A noticeable body weight loss was observed at days 12-16 and correlated with the peak of mucositis. As expected, the placebo gel did not show any effect regarding the development, the intensity and the duration of the mucositis. For the Amifostine IV group, the acute peak of mucosal reaction was also observed around day 15, but it was of lower intensity (score of 2.6 for the Amifostine IV group versus 6.4 for the control group) and mice recovered from the mucositis by the $30^{th}$ day. Interestingly, the same result as for the Amifostine IV group was observed for the Amifostine thiol gel group: the score at the peak was of 2.6 and mice did not show any signs of mucositis after day 30. So, the local application of the Amifostine thiol gel protected mice from radio-induced mucositis. With this gel, the mucositis was of lower intensity and duration.

G-Preclinical Evaluation of a Thermogel According to the Invention Containing Aminothiol for the Prevention of Radiation-Related Cutaneous Erythema Example G-1: Preparation of Gel Formulations by Reconstitution of Freeze-Dried Powder with Aqueous Solution for Efficacy Study The following formulations were used for an efficacy study with fractionated irradiation as explained hereafter. The freeze-dried thermogel were reconstituted the day before the efficacy study, stored at 5° C. and analyzed on dosing day.

Purity of amifostine batch used was taken into account and concentration in mg/ml is expressed as equivalent amifostine concentration.

| Formulation | Preparation method | Final composition % w/w |
|---|---|---|
| Gel n°10 Placebo Gel | Prepare the Placebo gel Freeze-drying the placebo gel Reconstitute freeze-dried powder using water to volume | Kolliphor P407: 21% Kolliphor P188: 4% Water 75% |
| Gel n°11 aminothiol at 25 mg/ml | Prepare the gel by mixing 8% v/v of a 500 mg/ml concentrated solution of amifostine previously converted into thiol (heating 1 h at 60° C. in HCl 4M) with 92% v/v of a placebo gel (P407/P188: 20/4) Freeze-drying the gel Reconstitution freeze-dried powder using water to volume | Amifostine 40 mg/ml converted in thiol (25 mg/ml) HCl 4M: ~8% Kolliphor P407: 18.4% Kolliphor P188: 3.7% Water: ~69.9% |

After reconstitution, final formulation Gels n°10 and 11 have the same composition as that before lyophilization, according to the invention.

Example G-2: Efficacy Study of the Gel Formulations of Example G-1

The aim of this example was to evaluate the efficacy of the thermogel compositions of example G-1 containing amifostine against radiation-induced cutaneous erythema in vivo.

Female C57BL/6 mice (12 weeks old) purchased from Janvier CERT (Le Genest St. Isle, France) were used after an acclimation time of 7 days. They had free access to food (SAFE reference R0340, Augy, France) and water. They were housed on a 12 hours light/dark cycle at a room temperature of 22° C.±2° C. and a relative humidity of 55%±15%.

Irradiation was carried out locally with a X-ray XRAD320 tube (320 kV, 12.5 mA) at a dose rate of 1.08 Gy/min, the rest of the body being protected by a lead shield. Only the skin on the back of mice was irradiated. Mice were euthanized when body weight loss exceeded 20% of the initial weight for more than 24 hours, in case of severe clinical signs or at the end of the experiment (ethical endpoints).

At high doses of irradiation, epidermal reactions (erythema, desquamation, ulceration, . . . ) are observed, beginning approximately 15 days after irradiation and reaching a peak about 20 days after irradiation. An arbitrary score system was used to evaluate the development of the radiation-induced cutaneous erythema.

Scoring Scale

|  | Score |
|---|---|
| normal | 0 |
| dry skin | 0.5 |
| cracking | 1 |
| one wound-slight desquamation | 2 |
| 2-3 non extended wounds (desquamation of <25% of irradiated area) | 3 |
| desquamation of <50% of irradiated area | 4 |
| desquamation of <75% of irradiated area | 5 |

Experiment

The purpose of this efficacy experiment was to evaluate the impact of Amifostine thiol on radiation-induced cutaneous erythema in a setting of a fractionated irradiation regimen and using reconstituted freeze-dried thermogels.

The experiment was conducted with a placebo gel and a gel containing 40 mg/ml Amifostine (corresponding to 25 mg/ml amifostine thiol). Four fractions of 12 Gy were delivered for four consecutive days (everyday from day 1 to day 4; day 1 corresponding to the first day of treatment) to the skin on the back of mice. The same amount of compound (corresponding to 4 mg amifostine per mouse) was administered to mice before each fraction of irradiation. Thus, the compound was applied 4 times for four consecutive days.

For each day, a similar experimental procedure was used. Briefly, mice were anesthetized, the Amifostine thiol gel or the placebo gel was applied directly onto the depilated skin on the back of mice 10 minutes later or not depending on the group (final volume of gel=100 µl). The gel was removed 1 hour later with water soaked compresses. Mice were then irradiated at a 12 Gy dose and awakened 10 minutes later. The same experimental procedure was repeated for 4 consecutive days.

Figure 4:
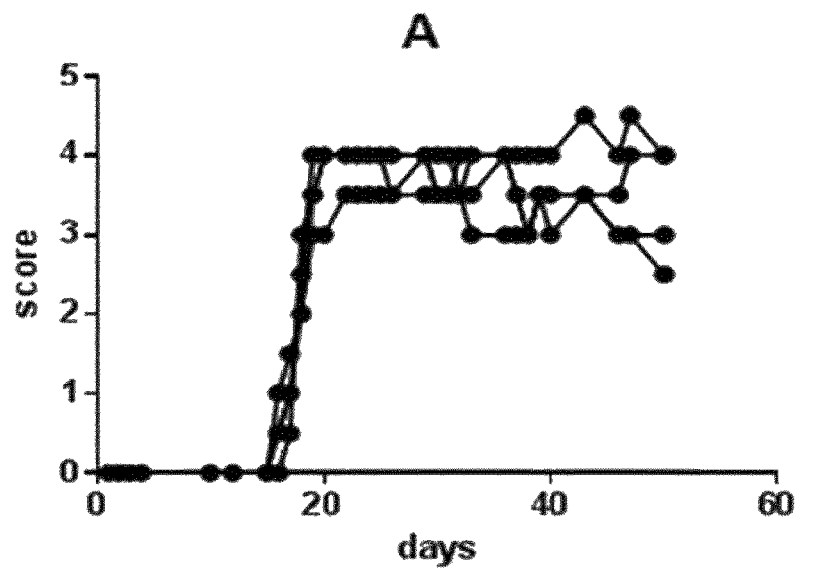
Figure 4:
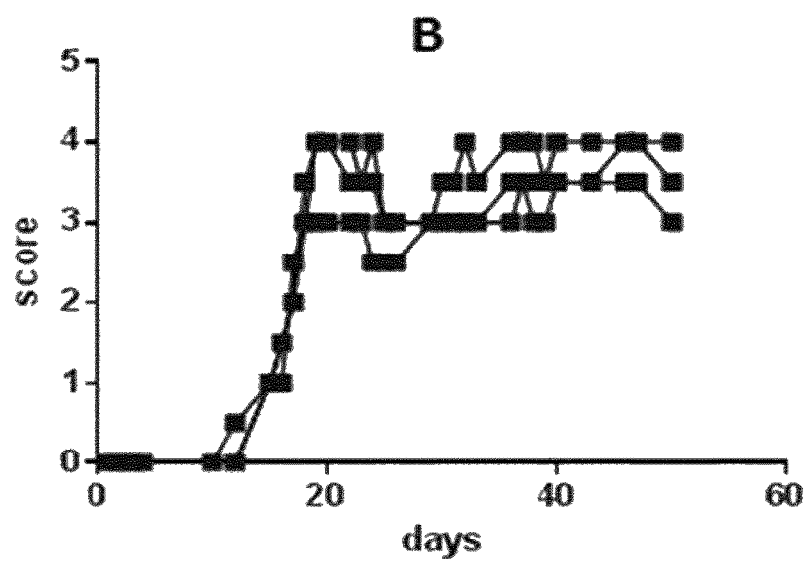
Figure 4:
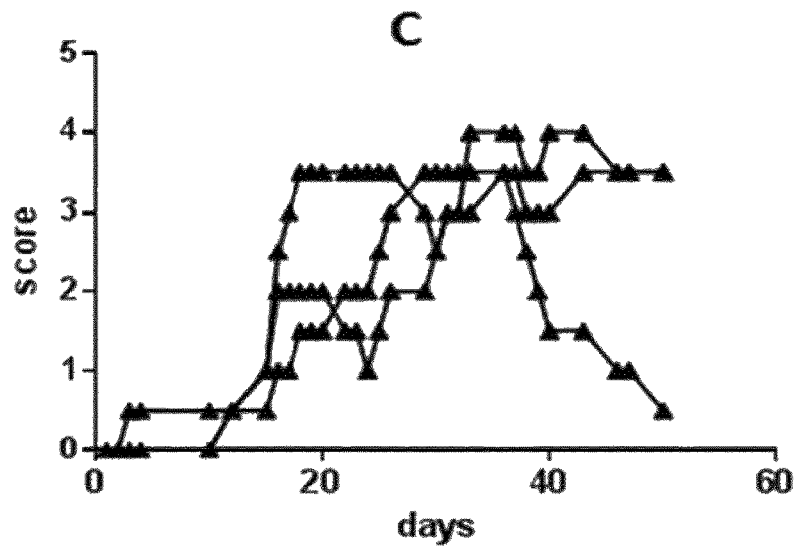

Ten mice were allocated to 3 groups:
Irradiation without gel (n=4 mice);
Irradiation with Amifostine thiol gel (Gel n°11) (25 mg/ml, corresponding to 4 mg amifostine or 2.5 mg amifostine thiol/mouse/day) (n=3 mice);
Irradiation with Placebo gel (Gel n°10) (n=3 mice);

For each group, the development of cutaneous erythema and body weight were analyzed daily (6 days/week) from day 3 to day 50. The epidermal reaction was monitored through macroscopic observation and scoring. Graphs depicting the evolution of the erythema score are presented in FIG. 4. Individual curves for the control group, the placebo gel (Gel n°10) group and the gel n°11 group are depicted in FIGS. 4A, 4B and 4C respectively.

In our experiment, mouse skin irradiation induced a severe desquamation with a peak of epidermal reaction around day 20. The desquamation reached a plateau and was still present at the end of the observation period. No body weight loss was observed during the course of the experiment. As expected, the placebo gel did not show any effect regarding the development, the intensity and the duration of the epidermal reaction. Interestingly, in the group of mice treated with the amifostine thiol gel, the development of erythema was delayed in 2 mice out of 3, and in this group, one mouse healed from the cutaneous reaction and recovered from the erythema by the $50^{th}$ day (score of 0.5 at day 50). So, the local application of the Amifostine thiol gel seems to protect mice from radio-induced erythema.

The invention claimed is:

1. A process for the preparation of freeze-dried 2-[(3-aminopropyl) amino]ethanethiol comprising the following steps:
    a) the reaction of a solution of amifostine with a strong acid, to obtain a solution of 2-[(3-aminopropyl)amino] ethanethiol, and
    b) the freeze-drying of the solution of 2-[(3-aminopropyl) amino]ethanethiol, with or without addition of excipients.

2. The process of claim 1, wherein the strong acid is chosen from the group consisting of: hydrochloric acid, phosphoric acid, sulfuric acid, and mixtures thereof.

3. The process of claim 1, wherein the strong acid is hydrochloric acid.

4. The process of claim 1, wherein step a) is carried out at a temperature comprised between 50° C. and 90° C.

5. The process of claim 1, wherein step a) is carried out for 30 minutes to 24 hours.

6. The process of claim 1, wherein the concentration of amifostine is comprised between 80 mg/ml and 500 mg/ml.

7. The process of claim 1, wherein the molarity of the acid is comprised between 1M and 4M.

8. The process of claim 1, wherein the molar ratio between the amount of amifostine and the amount of acid is comprised between 1:0.5 and 1:3.

9. The process of claim 1, further comprising a step a1), after step a) and before step b), for diluting the solution of 2-[(3-aminopropyl)amino]ethanethiol, with or without addition of excipients in the solution.

10. The process of claim 9, wherein step a1) consists in the addition of an aqueous solution comprising water or at least one poloxamer into the solution of 2-[(3-aminopropyl) amino]ethanethiol.

11. A lyophilisate of 2-[(3-aminopropyl)amino]ethanethiol susceptible to be obtained according to the process of claim 1.

12. A process for the preparation of a thermogel composition of 2-[(3-aminopropyl)amino]ethanethiol comprising the reconstitution of the lyophilisate of claim 11 with an aqueous solution, with or without addition of excipients.

13. The thermogel composition of 2-[(3-aminopropyl) amino]ethanethiol susceptible to be obtained according to the process of claim 12.

14. The thermogel composition of claim 13, for its use for treating or protecting mucosal or cutaneous tissue from damage associated with anticancer therapy.

15. The thermogel composition of claim 13, for its use for the treatment of radiation-induced oral mucositis.

16. The thermogel composition of claim 13, for its use for the treatment of radiation-induced cutaneous erythema.

* * * * *